United States Patent
Moffitt et al.

(10) Patent No.: US 9,339,643 B1
(45) Date of Patent: May 17, 2016

(54) ACUTELY STIFF IMPLANTABLE ELECTRODES

(75) Inventors: Michael A. Moffitt, Valencia, CA (US); Michael S. Colvin, Newbury Park, CA (US); Michael Onuscheck, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1969 days.

(21) Appl. No.: 11/694,769

(22) Filed: Mar. 30, 2007

(51) Int. Cl.
*A61N 1/00* (2006.01)
*A61N 1/05* (2006.01)
A61N 1/375 (2006.01)
A61N 1/04 (2006.01)

(52) U.S. Cl.
CPC .............. *A61N 1/05* (2013.01); *A61N 1/0476* (2013.01); *A61N 1/0553* (2013.01); *A61N 1/375* (2013.01)

(58) Field of Classification Search
CPC ............................. A61N 1/00; A61N 1/553
USPC ................... 607/115–126, 55–57
See application file for complete search history.

(56) References Cited

U.S. PATENT DOCUMENTS

| | | |
|---|---|---|
| 3,941,136 A | 3/1976 | Bucalo |
| 4,033,357 A | 7/1977 | Helland et al. |
| 4,135,518 A | 1/1979 | Dutcher |
| 4,301,815 A | 11/1981 | Doring |
| 4,475,560 A | 10/1984 | Tarjan et al. |
| 4,542,753 A | 9/1985 | Brenman et al. |
| 4,585,005 A | 4/1986 | Lue et al. |
| 4,628,944 A | 12/1986 | MacGregor et al. |
| 4,702,254 A | 10/1987 | Zabara |
| 4,722,353 A | 2/1988 | Sluetz |
| 4,796,643 A | 1/1989 | Nakazawa et al. |
| 4,867,164 A | 9/1989 | Zabara |
| 4,957,118 A | 9/1990 | Erlebacher |
| 5,025,807 A | 6/1991 | Zabara |
| 5,193,539 A | 3/1993 | Schulman et al. |

(Continued)

FOREIGN PATENT DOCUMENTS

| | | |
|---|---|---|
| WO | 98/37926 | 9/1998 |
| WO | 98/43700 | 10/1998 |
| WO | 98/43701 | 10/1998 |

OTHER PUBLICATIONS

Rattay, F., "Analysis of Models for External Stimulation of Axons," IEEE Transactions on Biomedical Engineering, Oct. 1986, BME-33(10): Title/Contents p. 974-977.

(Continued)

*Primary Examiner* — Eric D. Bertram
*Assistant Examiner* — Elizabeth K So
(74) *Attorney, Agent, or Firm* — Lowe Graham Jones PLLC; Bruce E. Black

(57) ABSTRACT

An implantable device for stimulating body tissue that includes an electrode lead body and at least one stimulating electrode contact disposed on the electrode lead body. The electrode lead body may be a percutaneous electrode lead or an electrode paddle that is configured and arranged to be substantially stiff outside the patient's body and during insertion into the patient's body and then becomes non-stiff within the patient's body. The stiffness may be modified using, for example, resorbable materials, temperature sensitive materials, or a lumen within the lead body for introducing a pressurized gas or liquid to modify a stiffness of the lead body. In one embodiment, the lead body may have different acute and/or chronic shapes.

5 Claims, 8 Drawing Sheets

(56) References Cited

U.S. PATENT DOCUMENTS

| | | |
|---|---|---|
| 5,193,540 A | 3/1993 | Schulman et al. |
| 5,312,439 A | 5/1994 | Loeb |
| 5,314,457 A | 5/1994 | Jeutter et al. |
| 5,376,108 A | 12/1994 | Collins et al. |
| 5,433,735 A | 7/1995 | Zanakis et al. |
| 5,439,938 A | 8/1995 | Snyder et al. |
| 5,454,840 A | 10/1995 | Krakovsky et al. |
| 5,480,420 A | 1/1996 | Hoegnelid et al. |
| 5,571,118 A | 11/1996 | Boutos |
| 5,741,319 A | 4/1998 | Woloszko et al. |
| 5,775,331 A | 7/1998 | Raymond et al. |
| 5,922,015 A | 7/1999 | Schaldach et al. |
| 5,938,584 A | 8/1999 | Ardito et al. |
| 6,051,017 A | 4/2000 | Loeb et al. |
| 6,058,332 A | 5/2000 | Dahl |
| 6,181,969 B1 | 1/2001 | Gord |
| 6,188,932 B1 | 2/2001 | Lindegren |
| 6,463,335 B1 | 10/2002 | Munch et al. |
| 6,516,227 B1 | 2/2003 | Meadows et al. |
| 6,600,956 B2 | 7/2003 | Maschino et al. |
| 6,609,029 B1 | 8/2003 | Mann et al. |
| 6,609,032 B1 | 8/2003 | Woods et al. |
| 6,650,943 B1 | 11/2003 | Whitehurst et al. |
| 6,735,474 B1 | 5/2004 | Loeb et al. |
| 6,741,892 B1 | 5/2004 | Meadows et al. |
| 6,788,975 B1 | 9/2004 | Whitehurst et al. |
| 7,003,352 B1 | 2/2006 | Whitehurst |
| 7,272,449 B2 * | 9/2007 | Dadd et al. ............ 607/137 |
| 2003/0236558 A1 | 12/2003 | Whitehurst et al. |
| 2004/0059392 A1 | 3/2004 | Parramon et al. |
| 2004/0249429 A1 * | 12/2004 | Tadlock ............ 607/116 |
| 2005/0004639 A1 * | 1/2005 | Erickson ............ 607/122 |
| 2005/0070982 A1 * | 3/2005 | Heruth et al. ............ 607/119 |
| 2006/0149335 A1 | 7/2006 | Meadows |
| 2006/0149336 A1 | 7/2006 | Meadows |
| 2006/0161204 A1 | 7/2006 | Colvin et al. |
| 2006/0184204 A1 | 8/2006 | He |
| 2006/0241737 A1 | 10/2006 | Tockman et al. |
| 2006/0247749 A1 | 11/2006 | Colvin |
| 2007/0129780 A1 | 6/2007 | Whitehurst et al. |
| 2007/0142889 A1 | 6/2007 | Whitehurst et al. |
| 2007/0150007 A1 | 6/2007 | Anderson et al. |
| 2007/0150036 A1 | 6/2007 | Anderson |
| 2007/0239243 A1 | 10/2007 | Moffitt et al. |
| 2008/0082141 A1 * | 4/2008 | Risi ............ 607/57 |
| 2008/0183224 A1 * | 7/2008 | Barolat ............ 607/2 |

OTHER PUBLICATIONS

U.S. Appl. No. 11/238,240, filed Sep. 9, 2005 (19 pages).

U.S. Appl. No. 11/376,360, filed Mar. 15, 2006 (14 pages).

Caparso, Anthony V. et al., "A Nerve Cuff Electrode for Controlled Reshaping of Neural Geometry," Proceedings of the Second Joint EMBS/BMES Conference (IEEE), Houston, Texas, Oct. 2002, 2054-2055.

Caparso, Anthony V. et al., "A Nerve Cuff Electrode for Controlled Reshaping of Nerve Geometry: Model and Experimental Results," 5 pages, https://www.ifess.org/ifess05/Poster%20Session%204/Caparso%20AV.htm (accessed Aug. 14, 2007).

U.S. Appl. No. 11/237,159, filed Sep. 28, 2005 (14 pages).

U.S. Appl. No. 11/241,156, filed Sep. 30, 2005 (20 pages).

* cited by examiner

ACUTELY STIFF IMPLANTABLE ELECTRODES

FIELD

The invention is generally directed towards electrode paddles and leads for neural stimulation, and more particularly but not exclusively to electrode paddles and leads that are acutely stiff outside of a patient's body and during insertion into the patient's body and subsequently becomes chronically flexible, or substantially non-stiff, within the patient's body.

BACKGROUND

Electrical stimulation of body tissues can be used for treatment of many different conditions and ailments, including treating pain. For example, pacemakers and implantable cardiac defibrillators have proven effective in the treatment of cardiac conditions. Spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation.

In many instances, an electrode lead or a paddle with one or more stimulating electrode contacts may be inserted into the body to position the electrode contacts near the tissue to be stimulated. In many instances, a stylet, such as a metallic wire, is inserted into a lumen running through the center of the lead from the proximal end to the distal end to aid in insertion of the lead into the body. The stylet is intended to provide lead stiffness during positioning and anchoring of the lead in the body. Once the lead is positioned, the stylet can be removed and the lead then becomes flaccid.

However, use of a stylet can have several limitations. For example, the stylet may perforate the lead assembly and may thereby damage the lead and/or body tissue. Further, a stylet may apply stiffness to a limited volume of the paddle or lead. Therefore, it is with respect to these considerations and others that the present invention has been made.

BRIEF SUMMARY

One embodiment is a device for stimulating tissue inside of a patient's body and includes an electrode paddle that is configured to be acutely stiff outside the patient's body and during insertion into the patient's body and then becomes chronically non-stiff within the patient's body. At least one stimulating electrode contact is disposed on the electrode paddle.

Another embodiment is a method for stimulating tissue inside of a patient's body. The method includes inserting an electrode lead into the patient's body. The electrode lead includes at least one stimulation electrode contact useable to stimulate a portion of the patient's body. The electrode lead further includes an internal lumen transitioning from a proximal end towards a distal end of the electrode lead. The method also includes making the electrode lead selectively pressurized to modify a stiffness of the electrode lead.

Yet another embodiment is a method for implanting a device into body tissue. The method includes inserting an electrode paddle into the body tissue. The electrode paddle includes at least one stimulation electrode contact for use in stimulating the body tissue. The electrode paddle is configured to maintain an acute substantially stiff configuration prior to and during insertion. After insertion into the body tissue, the method includes making the electrode paddle chronically non-stiff.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the invention may be embodied as methods or devices. The following detailed description is, therefore, not to be taken in a limiting sense.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Briefly stated the invention is directed towards an implantable device for stimulating body tissue and includes an electrode lead body and at least one stimulating electrode contact disposed on the electrode lead body. The electrode lead body may be an electrode lead, in one embodiment. In another embodiment, the electrode lead body may be an electrode paddle. In any event, the electrode lead body is configured and arranged to be substantially stiff outside the patient's body and during insertion into the patient's body and then becomes chronically non-stiff within the patient's body. The stiffness may be modified using, for example, resorbable materials, temperature sensitive materials, or a lumen within the lead body for introducing a pressurized gas or liquid to modify the temporal stiffness of the electrode lead body. In one embodiment, the electrode lead body may have different acute and/or chronic shapes.

Figure 8:
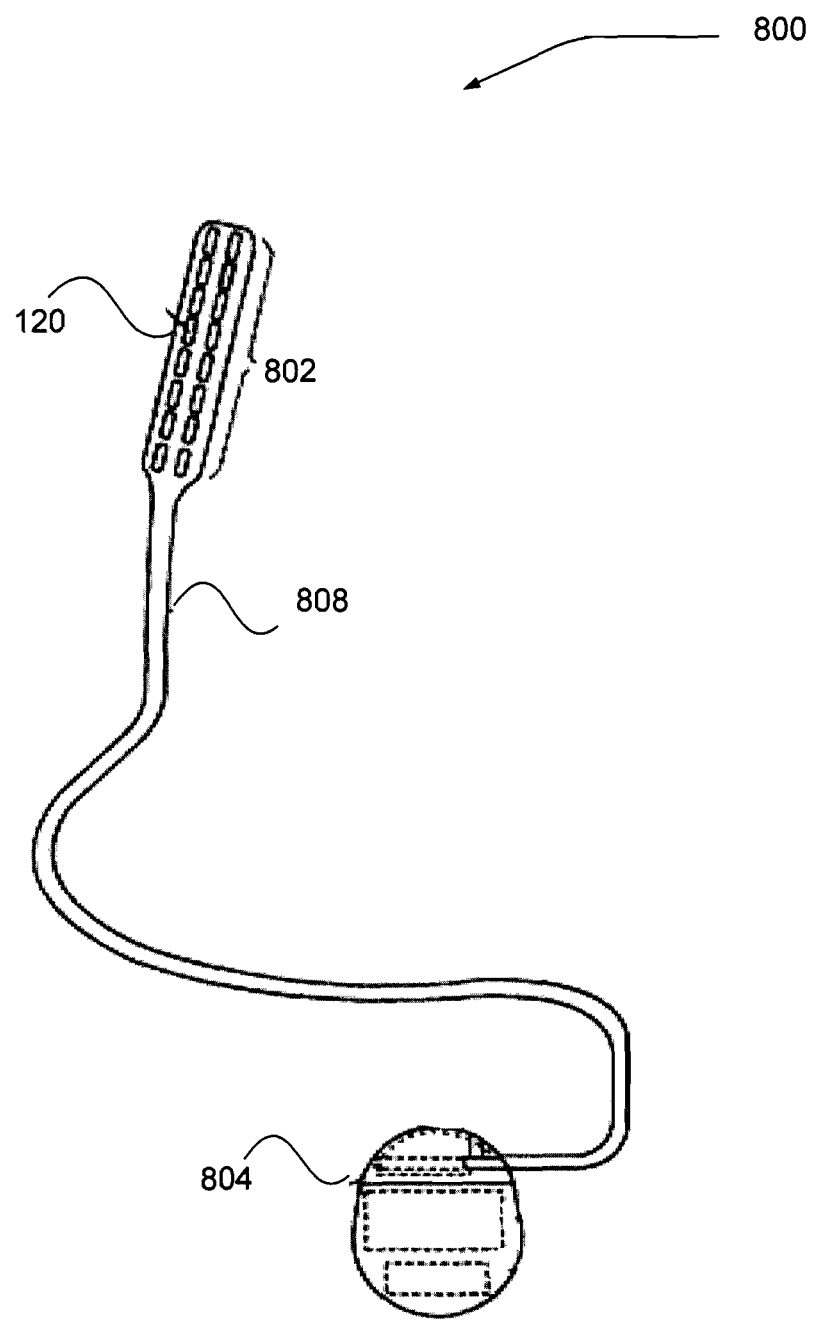
FIG. 8 shows one embodiment of an electrode paddle with a stimulation unit, in accordance with the invention.

FIG. 8 illustrates one embodiment of a stimulation system 800 that may be configured to provide electrical stimulation to selected nerves or other body tissue throughout a patient's body. As shown, stimulation system 800 includes an implantable electrode paddle 802, and a lead connector 808 for use in connection of the electrode contacts 120 to a control unit 804.

Examples of implantable electrode paddles are provided in U.S. patent application Ser. Nos. 11/376,360; 11/319,291; and 11/396,309, each of which is incorporated herein by reference. As indicated in U.S. patent application Ser. No. 11/319,291, the electrodes on an electrode paddle may be arranged in two or more parallel columns. However, the invention is not constrained to electrode paddles. For example, electrode cuff or electrode lead arrangements may also be employed. Examples of implantable electrode cuffs are provided in U.S. patent application Ser. Nos. 11/393,991, and 11/294,283, each of which is incorporated herein by reference.

The electrode contacts 120 may be arranged in any of a variety of configurations, other than that which is illustrated in FIG. 8. The electrode contacts 120 may be made of any of a variety of suitable body-compatible metal, alloy, conductive oxide, or other conductive material. Examples of suitable materials include platinum, iridium, platinum iridium alloy, stainless steel, titanium, or tungsten. Any type of electrode contact 120 can be used including monopolar electrodes, bipolar electrodes, and other multipolar electrodes. A variety of shapes can be used for the electrode contacts 120 including, for example, rings around the lead or electrodes in the form of circles, ovals, squares, rectangles, triangles, or the like, disposed on or within an electrode paddle layer 110, as shown in FIG. 1B.

In some embodiments, two or more different types of electrode contacts 120 can be provided including, for example, recording electrode contacts and stimulation electrode contacts. Examples of deep brain stimulation leads that include electrode contacts are provided in U.S. patent application Ser. Nos. 11/030,546; 11/230,052; 11/120,526; 11/237,159; and 11/241,156, each of which is incorporated herein by reference. Recording electrode contacts can be used, for example, to monitor insertion of the paddle or lead and determine where the tissue to be stimulated is located. Subsequently, the stimulation electrode contacts 120 can be used to stimulate the tissue. In some embodiments, the stimulation electrode contacts can also function as recording electrode contacts.

Examples of suitable control units 804 and lead connectors 808 include those described in U.S. Pat. Nos. 6,516,227, 6,609,029, and 6,741,892, each of which are incorporated herein by reference, as well as the Precision™ Spinal Cord Stimulation System available from Advanced Bionics Corporation, Sylmar, Calif., and/or other commercially available stimulator units.

Figure 1A:
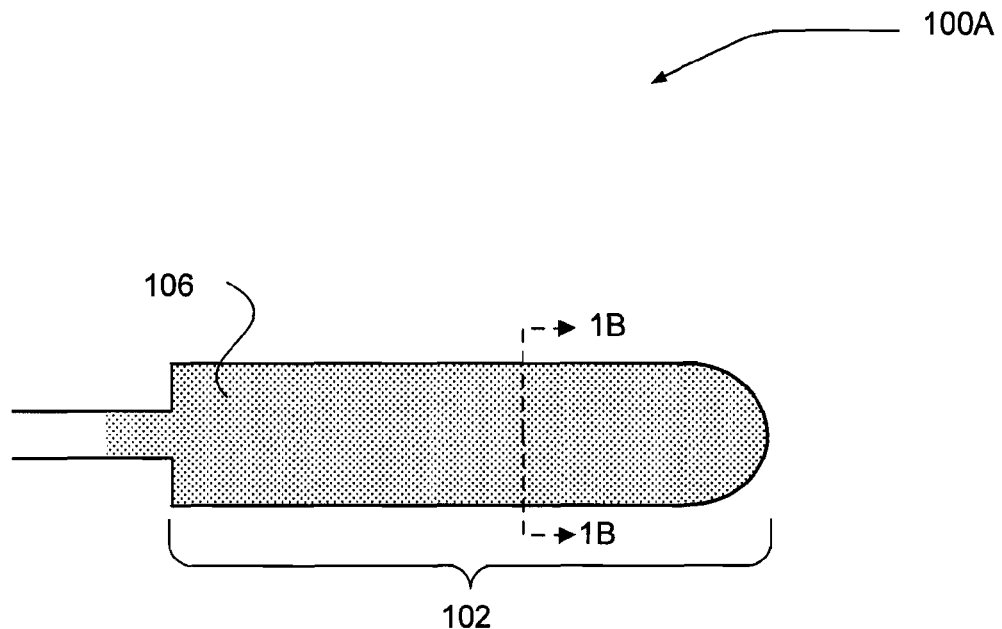
FIGS. 1A-1B show one embodiment of a top view of a paddle (1A) and a cross-sectional frontal view of the paddle (1B) having a resorbable material.
Figure 1B:
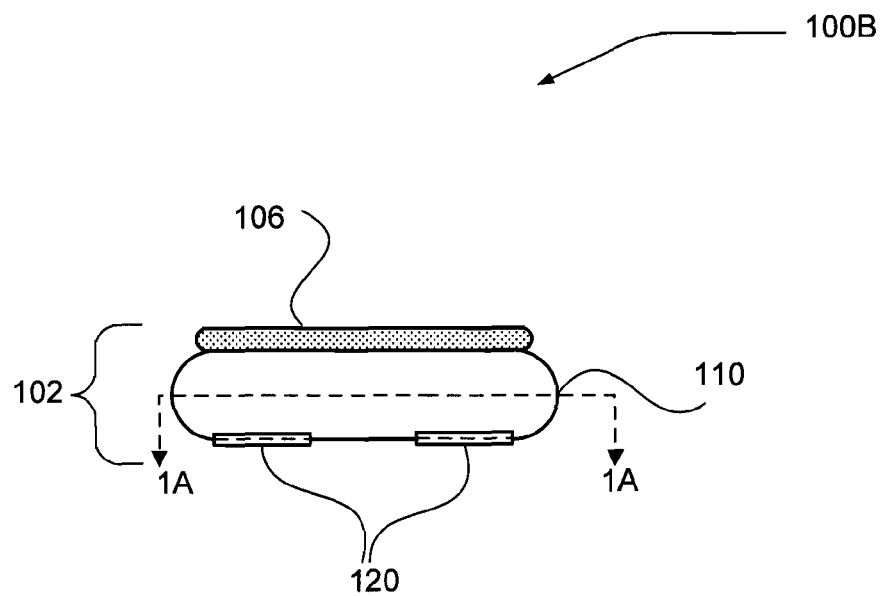

FIG. 1A illustrates one embodiment of a top view of an implantable electrode paddle 102, having resorbable material 106. Electrode contacts 120 (shown in FIG. 1B's cross-sectional view, are not illustrated in FIG. 1A, for clarity). The resorbable material 106 provides stiffness during the implantation of electrode paddle 102 into a patient's body. After implantation, the resorbable material 106 may be absorbed into the body to provide a chronically non-stiff or flexible electrode paddle 102.

FIG. 1B illustrates a cross-sectional frontal view of the implantable electrode paddle 102, showing electrode contacts 102, electrode paddle layer 110 with resorbable material 106. In one embodiment, resorbable material 106 may be configured as a coating layered upon electrode paddle 102. However, the invention is not so limited, and resorbable material 106 may be integrated within at least a portion of electrode paddle layer 110.

Electrode paddle layer 110 may be constructed from any of a variety of suitable body compatible non-conductive substrate flexible or non-stiff material, including but not limited to, silicone, polyurethane, Silastic™, or the like, wherein one or more electrode contacts 120 may be placed on or within at least one major surface.

Also shown in FIG. 1A is one embodiment of a layer of resorbable material 106 on electrode paddle 102. Such resorbable material 106 arrangement allows the implantable electrode paddle 102 to maintain a stiff configuration when it is outside of a patient's body and during insertion into the body. However, the electrode paddle 102 may then become chronically non-stiff or flexible upon extended exposure inside of the patient's body. The transition from the acute substantially stiff state to the chronic flexible or non-stiff state may be achieved by absorption of the resorbable material 106 by the body of the patient over time. The transition time from a stiff state to a non-stiff or flexible state should be sufficient to allow a physician to implant and position the electrode paddle 102.

Moreover, a degree of stiffness may be based on a variety of factors. For example, the acute substantially stiff state may be determined based on being sufficiently stiff to enable a physician to implant the electrode lead body within a patient, while being adequately flexible to accommodate its shape to the patient's anatomy, so as to minimize harm to the patient due to being excessively rigid.

The resorbtion time for the resorbable material 106 can be based on one or more factors, such as, for example, the implantable device, a site of implantation, an expected lifetime of the implantable device, an expected duration of implantation, an age of the patient, expected growth rate of tissue around the implanted device, or a variety of other factors. It will be recognized that there may be a substantial variation from an average resorbtion time in actual devices. Thus, actual resorbtion times may depend on the conditions within the patient's body.

Examples of suitable resorbable materials include, but are not limited to, a copolymer, including polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester)s (POEs), polycyanoacrylate, polyphosphazene, modified polysaccharides (for example, cellulose, chitin, dextran), and modified proteins (for example, fibrin, casein). Moreover, the resorbable material 106 may include a combination of one or more of possible substances.

In some embodiments, the resorbable material 106 may also have a drug, medication, tissue growth enhancer, or other agent disposed within and/or on the resorbable material for time release. For example, the resorbable material 106 may be combined with a drug or other medication to treat the tissue at the implantation site or to reduce pain or inflammation. As another example, the resorbable material 106 may be combined with a substance that promotes tissue growth and encapsulation of at least a portion of the implantable device. Generally, the drug, medication, or other agent is released over time as the resorbable material 106 is resorbed by the patient's body.

In another embodiment, the resorbable material 106 may be replaced with a temperature sensitive material that is acutely stiff at a nominal room temperature and transitions to a chronically non-stiff or flexible material at a nominal body temperature so that the material is substantially flaccid at body temperature. In one embodiment, the temperature sensitive material transitions to chronically non-stiff or flexible in a temperature range that begins at or above room temperature, but below body temperature, and ends below, at, or above body temperature. For example, in one embodiment, the temperature sensitive material may be acutely stiff at a temperature of about 25° C., non-stiff at about 37° C., and may be configured to transition from acutely stiff to chronically non-stiff over a temperature range lying between these two temperatures.

In another embodiment, the temperature sensitive material may also be integrated into the lead material.

In one embodiment, the temperature sensitive material may be made of a plastic material that has a glass transition temperature ($T_g$) that is near or less than a nominal body temperature. Preferably, the glass transition temperature is greater than room temperature, but in some embodiments the glass transition temperature can be less than or equal to room temperature. In one embodiment, the glass transition temperature of the temperature sensitive material is in a range of between about 25° C. to about 38° C. In one embodiment, the implantable electrode paddle 102 may be stored in or temporarily submitted to a sufficiently cold environment prior to insertion.

The temperature sensitive material may include a polymer which can be a homopolymer, a copolymer formed using two or more different monomeric units, or a mixture of polymers. The temperature sensitive material can also include additives such as filler, colorants, anti-oxidants, and the like. In particular, plasticizer additive(s) can be particularly useful to modify the glass transition temperature of the base polymer or mixture of polymers.

The selection of a suitable glass transition temperature and temperature sensitive material can be based on one of more factors including, but not limited to, biocompatibility, cost, ease of manufacture, stability, glass transition temperature of the temperature sensitive material, heat capacity of the temperature sensitive material, thermal mass of the electrode lead body (paddle or lead), type of tissue to be stimulated, the depth of the tissue to be stimulated, thickness of the electrode lead body, flexibility of the electrode lead body material, and the like. The electrode lead body should remain sufficiently stiff during insertion of the electrode lead body into the body to allow the electrode lead body to be positioned without becoming too flexible or non-stiff. The rapidity with which the electrode lead body increases temperature will be determined, at least in part, by the heat capacity and thermal mass of the electrode lead body. Thus, an electrode lead body with a relatively low glass transition temperature, low heat capacity, and small thermal mass will typically become non-stiff prior to a lead with higher glass transition temperature, higher heat capacity, and larger thermal mass.

In one embodiment, the temperature sensitive material may be configured as a layer of material over the electrode paddle layer 110. However, the invention is not so limited. For example, in one embodiment, electrode paddle layer 110 may be configured from the temperature sensitive material such that the electrode paddle layer 110 becomes acutely stiff at temperatures below the nominal body temperature, and upon returning to the nominal body temperature, becomes chronically non-stiff or flexible.

Although an implantable electrode paddle configuration is illustrated in FIGS. 1A-1B, the invention is not so limited. Thus, for example, resorbable layer 106, and/or temperature sensitive materials may also be employed with other electrode lead body configurations. For example, in one embodiment, a percutaneous lead may also be configured to employ one or more of mechanisms to modify its stiffness, without departing from the scope of the invention.

Modifying the stiffness of an electrode lead body (e.g., an electrode paddle, or percutaneous lead) may also be achieved employing an internal lumen that is configured for receiving a liquid, gas, or similar substance. Thus, FIGS. 2A-2B show one embodiment of another top view of an electrode paddle (FIG. 2A) and a cross-sectional frontal view of the electrode paddle (FIG. 2B).

Figure 2A:
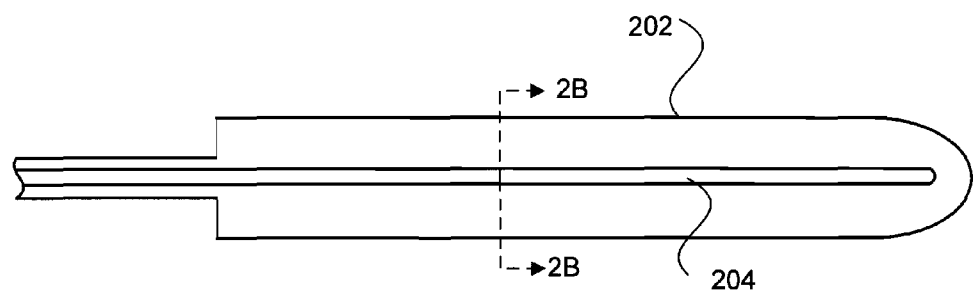
FIGS. 2A-2B show one embodiment of another top view of a paddle (2A) and a cross-sectional frontal view of the paddle (2B) having an internal lumen useable for providing temporal stiffness of the paddle using pressurization.
Figure 2B:
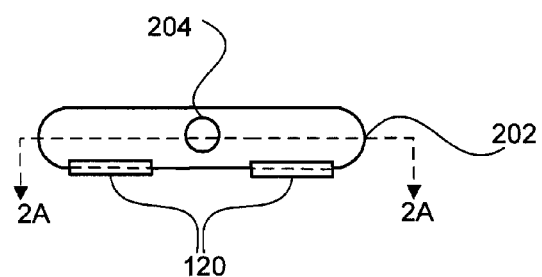

As shown in FIGS. 2A-2B, electrode paddle 202 includes an internal lumen 204 useable for providing temporal stiffness of the paddle using pressurization. Internal lumen 204 may be configured to receive a liquid and/or a gas. The presence of the liquid and/or gas modifies an internal pressure within the lumen and thereby results in modifying a stiffness of electrode paddle 202. In one embodiment, the addition of the liquid and/or gas into internal lumen 204 modifies the electrode paddle 202 from a non-stiff or flexible arrangement to a stiff arrangement. Upon implantation of electrode paddle 202 into a patient's body, at least a portion of the liquid and/or gas may be removed, thereby reducing the pressure and thus producing the chronic non-stiff or flexible arrangement.

Figure 3A:
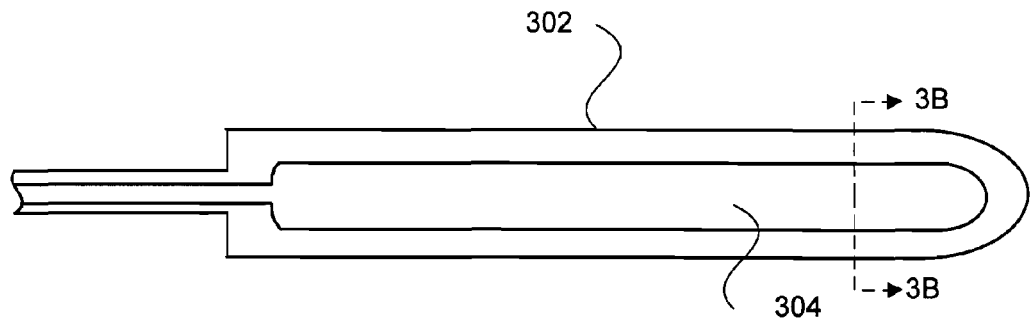
FIGS. 3A-3B show another embodiment of a view of a paddle top (3A) and a cross-sectional frontal view of the paddle (3B) having an internal lumen useable for providing temporal stiffness of the paddle using pressurization.
Figure 3B:
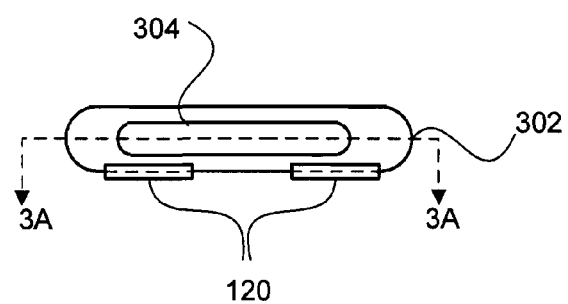

In one embodiment, internal lumen 204 is configured as a single lumen within electrode paddle 202 transitioning linearly from a proximal end to a distal end of the electrode paddle 202 along a longitudinal axis of electrode paddle 202. In one embodiment, the internal lumen 204 may be cylindrical in shape. However, the invention is not so limited, and other shapes may be employed. Thus, for example, shown in FIGS. 3A-3B are views of one embodiment of an electrode paddle 302 having an internal lumen 304 with an oblong cross-section. Thus, internal lumens may have an oval shape, oblong shape, or any of a variety of other shapes. Moreover, in one embodiment internal lumen 304 may have a first portion having a first shape, and at least one other portion having at least a second shape.

Figure 4A:
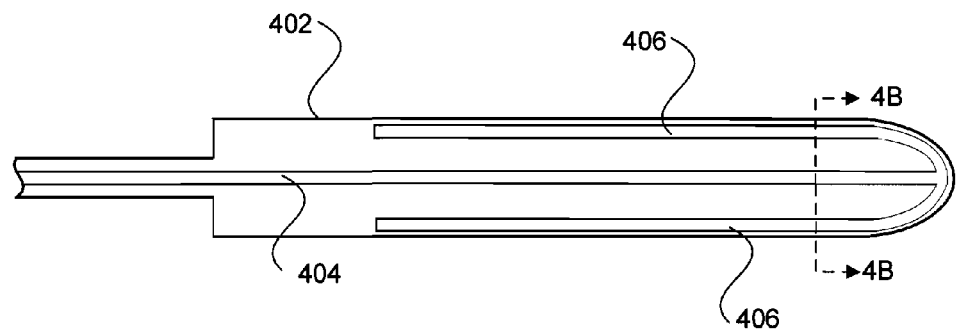
FIGS. 4A-4B show one embodiment illustrating another view of a paddle top (4A) and a cross-sectional frontal view of the paddle (4B) having an internal lumen with branches.
Figure 4B:
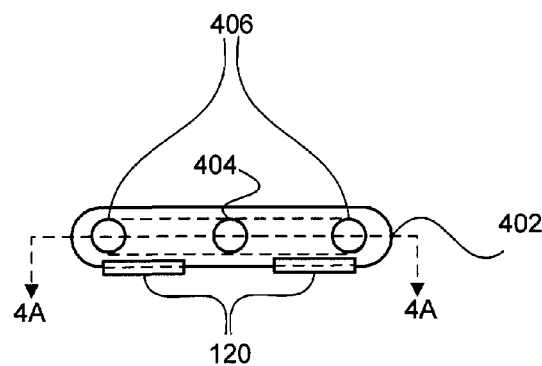

In another embodiment, the internal lumen may include branches. For example, FIGS. 4A-4B show another embodiment of views of an electrode paddle 402 having an internal lumen with branches. As shown, the internal lumen includes a first portion 404 that transitions within electrode paddle 402 longitudinally from a proximal end to a distal end of the electrode paddle 402. At the distal end of the internal lumen, the internal lumen divides into branches 406, where the branches 406, are arranged to circle back internally within electrode paddle 402. In one embodiment, branches 406 may transition longitudinally back towards the proximal end of the electrode paddle 402. In one embodiment, branches 406 may extend longitudinally within the electrode paddle 402, along opposing sides within the electrode paddle 402. In one embodiment, the branches 406 may traverse an entire length of the electrode paddle 402. In another embodiment, the branches 406 may traverse less than the entire length of the electrode paddle 402.

Figure 4C:
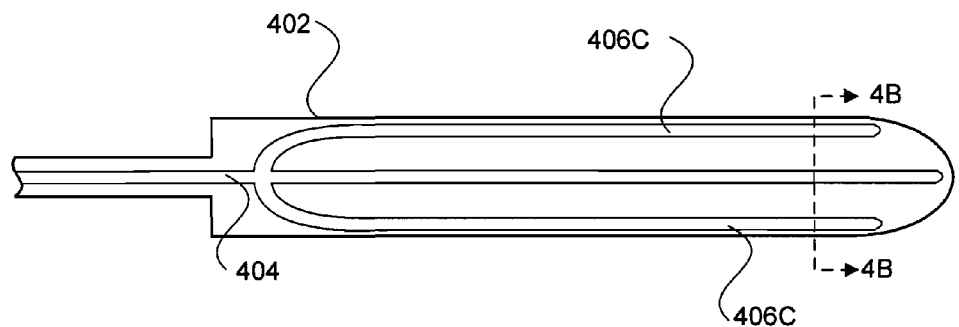
FIG. 4C shows another embodiment illustrating a view of a paddle top having an internal lumen with branches.

However, internal lumens with branches may also be configured with branches that branch closer to a proximal end of the electrode paddle 402. Thus, another embodiment of an internal lumen with branches is illustrated in FIG. 4C. As shown, branches 406C may divide outward from the first portion 404 near the proximal end of electrode paddle 402, and extend towards the distal end of the electrode paddle 402, along opposing sides within the electrode paddle 402. Employing the opposing branches, such as those illustrated in FIG. 4A-4C, provides stiffness to the central portion of the electrode paddle 402, as well as along the peripheral portions of the electrode paddle 402.

Figure 5A:
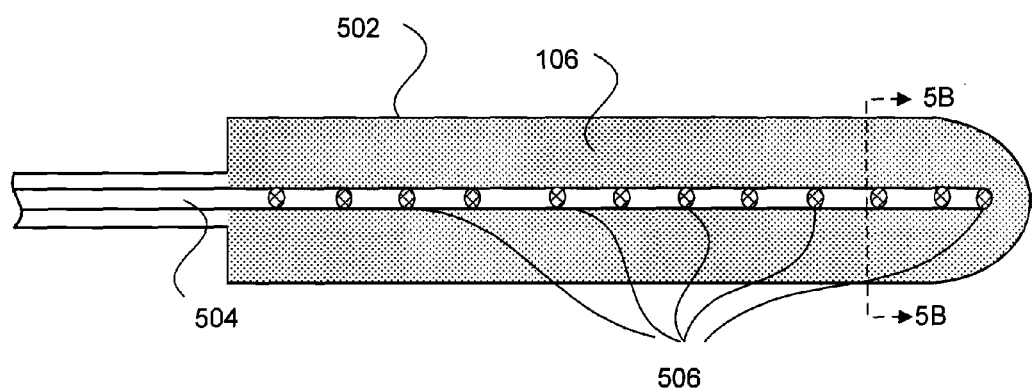
FIGS. 5A-5B show one embodiment a view of a paddle top (5A) and a cross-sectional frontal view of the paddle (5B) having an internal lumen with external ports.
Figure 5B:
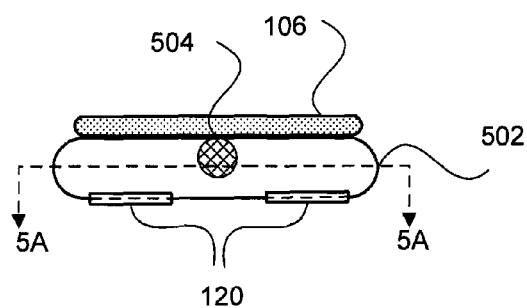

In another embodiment, FIGS. 5A-5B show views of an electrode paddle 502 having an internal lumen 504 with external ports 506. In one embodiment, internal lumen 504 may be employed in conjunction with a resorbable material 106, such as described above in conjunction FIGS. 1A-1B. In one embodiment, the external ports 506 are holes that enable a solvent or other substance to be injected from internal lumen 504 into the resorbable material. In one embodiment, the solvent may be used to assist in degrading the resorbable material. Such solvents may be employed to modify the resorbtion rate of the resorbable material. This may be desirable, for example, where the electrode paddle (or electrode lead) is implanted in a body area surrounded by fat in an epidural space, or the like, that may negatively impact the resorbtion rate. In one embodiment, the solvent may include, for example, a saline solution, or other biocompatible solution. In one embodiment, the internal lumen 504 may also contain a resorbable material that may be resorbed through external ports 506 to the tissue side. In another embodiment, internal lumen 504 may be used to inject a material to change the temperature of electrode paddle 502. For example, in one embodiment, a warm saline solution may be injected through internal lumen 504 after placement of electrode paddle 502 to initiate transition to an acutely non-stiff state. In another embodiment, external ports 506 may also be employed to introduce a medication to the body area.

Figure 6A:
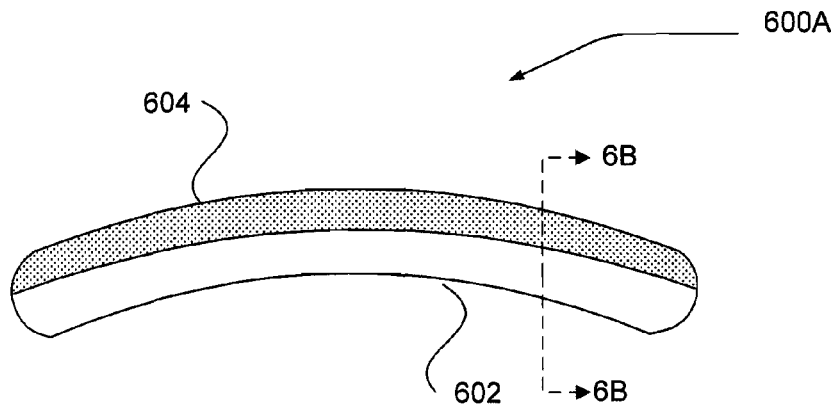
FIGS. 6A-6B show one embodiment of another paddle in an acute configuration (6A) and a chronic configuration (6B)
Figure 6B:
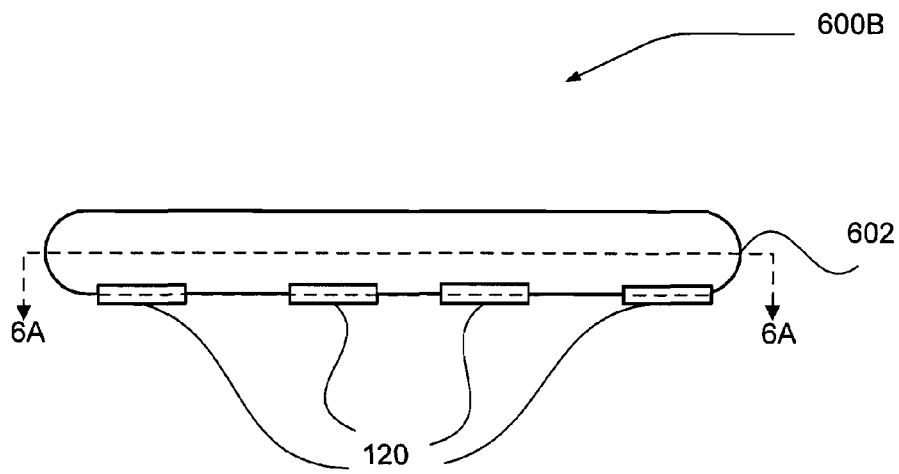

It may be desirable to have the implantable electrode paddle or lead maintain one shape acutely to facilitate implantation, and a different shape chronically to facilitate stimulation of tissue. For example, in one embodiment, an acute shape may be selected that fits a patient's anatomy, a nerve structure, or the like. In one embodiment, the chronic shape may be selected for placement of the stimulating electrode contacts within a desired range of a target tissue. Thus, as shown in FIGS. 6A-6B are one embodiment of another electrode paddle 602 in an acute configuration 600A (see FIG. 6A) and a chronic configuration 600B (see FIG. 6B). The acute configuration of electrode paddle 602 may, in one embodiment, be obtained by the use of shaped resorbable material 604. As the shaped resorbable material 604 is resorbed, electrode paddle 602 may take on the chronic configuration. Moreover, in one embodiment, electrode paddle 602 may employ a temperature sensitive material, such as described above, in addition to, or in place of the resorbable material 604.

Figure 7A:
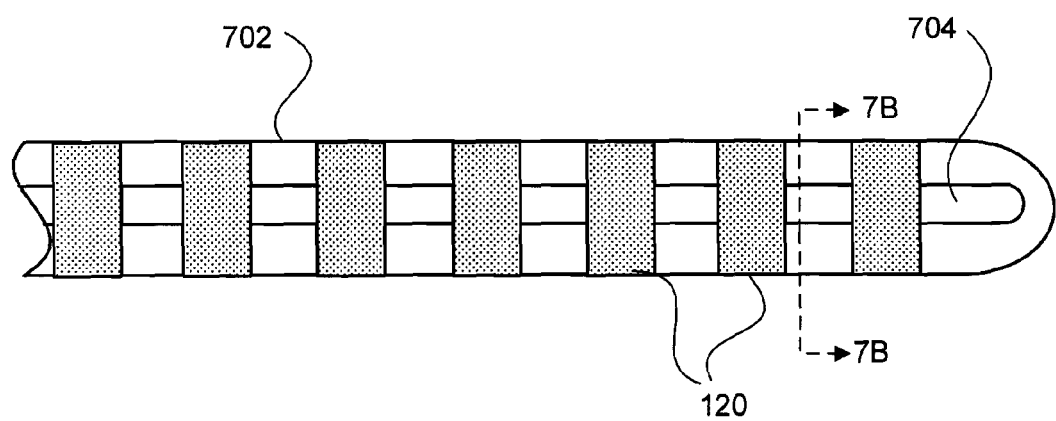
FIGS. 7A-7B show one embodiment of an electrode lead having a lumen that can be pressurized to modify a stiffness of the electrode lead.
Figure 7B:
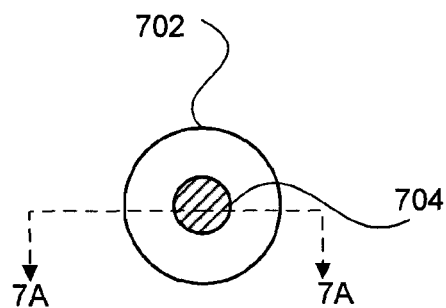

As discussed above, embodiments of the invention are not limited to electrode paddles. Thus, FIGS. 7A-7B show one embodiment of an electrode lead 702 having an internal lumen 704 that can be pressurized to modify a stiffness of the electrode lead 702. Internal lumen 704 may be configured to transition longitudinally from a distal end to a proximal end within electrode lead 702.

A liquid and/or gas may be employed within internal lumen 704 to pressurize internal lumen 704, and thereby maintain an acute substantially stiff configuration outside of and during insertion into the patient's body. Release of the pressure within internal lumen 704 is directed towards making the electrode lead 702 chronically non-stiff or flexible within the patient's body.

Thus, in one example of a method of using the selectively stiff electrode body, access to the desired position in the body can be accomplished by opening a hole through the patient's skin. The point of entry, as well as whether a hole may be made in other tissues prior to inserting the selectively stiff electrode body, will depend on the application. The selectively stiff electrode body, which is acutely stiff, can be inserted into the tissue. The selectively stiff electrode body can be guided to the target location within the body while it maintains sufficient stiffness. The optional recording electrode(s) can be observed using an external control unit to identify the target tissue, if desired. Once in place, the selectively stiff electrode body can be positioned and, if desired, anchored using any of a variety of mechanisms. The selectively stiff electrode body then becomes chronically non-stiff or flexible based on the mechanism employed, as described above.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A device for stimulating tissue inside a patient's body, comprising:
an electrode paddle that is configured to be acutely stiff outside the patient's body and during insertion into the patient's body and then becomes chronically non-stiff within the patient's body, wherein the electrode paddle comprises an internal lumen transitioning from a proximal end towards a distal end of the electrode paddle along a longitudinal axis of the electrode paddle, wherein the internal lumen is configured and arranged to be pressurized with a liquid or gas to modify the electrode paddle to be acutely stiff, and wherein after implantation into the patient's body, the pressure can be released to enable the electrode paddle to become chronically non-stiff, wherein the internal lumen comprises a plurality of branches within the electrode paddle and the internal lumen is sealed except at one opening at the proximal end of the electrode paddle through which the internal lumen can be pressurized with the liquid or gas; and
a plurality of stimulating electrode contacts disposed on the electrode paddle in at least two adjacent columns, each column comprising a plurality of the stimulation electrode contacts.

2. The device of claim 1, wherein the branches extend within the electrode paddle along opposing sides of the internal lumen within the electrode paddle.

3. A method for stimulating tissue inside of a patient's body, the method comprising:
- inserting the device of claim 1 into the patient's body; and
- making the electrode paddle selectively pressurized to modify a stiffness of the electrode paddle.

4. The method of claim 3, wherein making the electrode paddle selectively pressurized further comprises introducing into the internal lumen at least one of a liquid or a gas.

5. The method of claim 3, wherein making the electrode paddle selectively pressurized further comprises:
- pressurizing the internal lumen such that the electrode paddle becomes acutely stiff;
- releasing the pressure after implantation into the patient's body to enable the electrode paddle to become chronically non-stiff.

* * * * *